United States Patent
Spahn

(10) Patent No.: US 10,426,415 B2
(45) Date of Patent: Oct. 1, 2019

(54) METHOD FOR RECEIVING ENERGY-SELECTIVE IMAGE DATA, X-RAY DETECTOR AND X-RAY SYSTEM

(71) Applicant: Martin Spahn, Erlangen (DE)

(72) Inventor: Martin Spahn, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 639 days.

(21) Appl. No.: 15/196,658

(22) Filed: Jun. 29, 2016

(65) Prior Publication Data

US 2017/0000431 A1 Jan. 5, 2017

(30) Foreign Application Priority Data

Jun. 30, 2015 (DE) .......................... 10 2015 212 155

(51) Int. Cl.
*A61B 6/00* (2006.01)
*G01T 1/29* (2006.01)

(52) U.S. Cl.
CPC .......... *A61B 6/4241* (2013.01); *A61B 6/5205* (2013.01); *G01T 1/2928* (2013.01); *A61B 6/4042* (2013.01); *A61B 6/4233* (2013.01); *A61B 6/461* (2013.01); *A61B 6/487* (2013.01)

(58) Field of Classification Search
CPC ... A61B 6/4042; A61B 6/4233; A61B 6/4241; A61B 6/461; A61B 6/487; A61B 6/5205; G01T 1/2928
See application file for complete search history.

(56) References Cited

U.S. PATENT DOCUMENTS

| 2014/0016748 A1* | 1/2014 | Spahn ..................... G01T 1/247 378/62 |
| 2014/0185781 A1 | 7/2014 | Reitz et al. |
| 2014/0270073 A1 | 9/2014 | Spahn |

FOREIGN PATENT DOCUMENTS

| DE | 2758495 A1 | 7/1978 |
| DE | 102012212124A1 A1 | 1/2014 |
| DE | 102013200021 A1 | 7/2014 |
| DE | 102013204264 A1 | 9/2014 |

OTHER PUBLICATIONS

German office Action for related German Application No. 10 2015 212 155.0 dated Apr. 26, 2016, with English Translation.
Spahn Martin, "Flat detectors and their clinical applications", European Radiology, vol. 15, 2005, pp. 1934-1947, DOI:10.1007/s00330-005-2734-9.

(Continued)

*Primary Examiner* — Chih-Cheng Kao
(74) *Attorney, Agent, or Firm* — Lempia Summerfield Katz LLC

(57) ABSTRACT

A method and system for receiving energy selective image data relating to an examination object using a counting, digital X-ray detector, together with a counting, digital X-ray detector and an X-ray system are provided. The X-ray detector includes an X-ray converter for direct or indirect conversion of X-rays into an electrical signal, and a matrix including a plurality of counting pixel elements. For each pixel element of the plurality of counting pixel elements, at least one modifiable threshold value, above which an incoming signal is counted using a memory unit, is applicable.

18 Claims, 12 Drawing Sheets

(56) References Cited

OTHER PUBLICATIONS

Wong, Winnie, "A Hybrid Pixel Detector ASIC with Energy Binning for Real-Time, Spectroscopic Dose Measurements" Dissertation, Institutionen för informationsteknologi och medier MITTUNIVERSITETET, 2012 http://www.miun.se/siteassets/forskning/center-och-institut/stc/abstracts/2012.dissertation-winnie-wong.pdf.

German Research Report for German Application No. 102015212155.0, dated Aug. 16, 2018.

* cited by examiner

METHOD FOR RECEIVING ENERGY -SELECTIVE IMAGE DATA, X-RAY DETECTOR AND X-RAY SYSTEM

CROSS-REFERENCE TO RELATED APPLICATIONS

This application claims the benefit of DE 10 2015 212 155.0, filed on Jun. 30, 2015, which is hereby incorporated by reference in its entirety.

TECHNICAL FIELD

Embodiments relate to receiving energy selective image data relating to an examination object using a counting digital X-ray detector.

BACKGROUND

For diagnostic examination and for interventional procedures, for example, in cardiology, radiology, and also in surgery, X-ray systems are used for imaging. X-ray systems 16, as shown in FIG. 1, include an X-ray tube 18 and an X-ray detector 17, for example, arranged together on a C-arm 19, a high voltage generator to generate the tube voltage, an imaging system 21 (e.g., including at least one monitor 22), a system control unit 20, and a patient couch 23. Systems with two planes (e.g., two C-arms) are likewise used in interventional radiology. Flat panel X-ray detectors may be used as X-ray detectors in many areas of medical X-ray diagnostics and intervention (e.g., in radiography, interventional radiology, cardiac angiography), and also for imaging in therapy in the context of monitoring and planning of radiation or for mammography.

Present day flat panel X-ray detectors may be integrating detectors and may be based on scintillators that convert X-ray beams into comparatively low-energy radiation, for example, into visible light. This light is converted into an electrical charge in matrices of photodiodes. The matrices are then read line by line via active control elements. FIG. 2 shows the basic design in current use of an indirectly converting flat panel X-ray detector, including a scintillator 10, an active readout matrix 11 made of amorphous silicon with a plurality of pixel elements 12 (with a photodiode 13 and a switch element 14), and control and readout electronics 15 (see, for example, M. Spahn, "Flat detectors and their clinical applications," Eur Radiol. (2005), 15: 1934-1947).

Depending on the quality of the beam, the quantum efficiency for a scintillator made of CsI with a layer density of, for example, 600 m is between 50% and 80% (see, for example, M. Spahn, "Flat detectors and their clinical applications," Eur Radiol (2005), 15: 1934-1947). The local frequency dependent DQE(f) detective quantum efficiency has an upward limit as a result thereof and for certain pixel sizes of, for example, 150 to 200 □m, and, for the local frequencies of interest for practical applications of 1 to 2 lp/mm, falls well below this limit. In order to allow new applications (e.g., dual energy, material separation), but also to further increase the quantum efficiency, the potential of counting detectors or energy discriminating counting detectors mainly based on directly converting materials (e.g., CdTe or CdZnTe=CZT) and of ASICs with contacts (application specific integrated circuits such as a CMOS technology design) is increasingly used. Other materials such as Si or GaAs may likewise be of interest for specific applications.

An example of a design for such counting X-ray detectors is shown in FIG. 3. X-rays are converted in the direct converter 24 (e.g., CdTe or CZT), and the charge carrying pairs that are generated are separated via an electric field that is generated by a shared top electrode 26 and a pixel electrode 25. In one of the pixelated pixel electrodes 25 of the ASIC 27, the charge generates a charge pulse, the level of which corresponds to the energy of the X-ray quantum and that, if the charge pulse is above a defined threshold value, is recorded as a counting event. The threshold value serves the purpose of distinguishing an actual event from electronic noise or, for example, suppressing k fluorescence photons in order to avoid multiple counts. The ASIC 27, a corresponding section of the direct converter 24, and a coupling between the direct converter 24 and the ASIC 27 (e.g., in directly converting detectors using bump bonds 36) each form a detector module 35 with a plurality of pixel elements 12. The ASIC 27 is arranged on a substrate 37 and is connected to peripheral electronics 38. A detector module 35 may also include one or a plurality of ASICs 27 and one or a plurality of parts of a direct converter 24, selected as required.

FIG. 5 shows the general layout of a counting pixel element 12. The electrical charge is collected via the charge input 28 in the pixel element 12 where the electrical charge is amplified with the aid of a charge amplifier 29 and a feedback capacitor 40. In addition, on the output, the pulse shape may be adjusted in a pulse shaper (e.g., filter) (not shown). An event is then counted by moving a digital memory unit 33 (e.g., a meter or counter) up by one when the output signal is above a settable threshold value. This is established via a discriminator 31. In principle, the threshold value may also be provided in analog form, but is currently applied via a digital to analog converter (DAC) 32 and is thus variably adjustable within a certain range. The threshold value may either be adjustable locally on a pixel by pixel basis, as shown via the (local) discriminator 31 and the (local) DAC 32 or globally for a plurality of/all pixel elements via, for example, a global discriminator and DAC. The readout may subsequently ensue via a control and readout unit or peripheral electronics 38.

In addition to a global DAC that serves, for example, to adjust a specific keV threshold for an entire detector module or the entire X-ray detector, a further pixel by pixel adjustment that is intended to correct pixel to pixel fluctuations (e.g., fluctuations of amplifiers 29, local material non homogeneities in the detector material, etc.) may be necessary. This pixel by pixel calibration or correction DAC may have a considerably higher resolution than the global DAC and is adjustable, for example, across a keV range within which pixel to pixel fluctuations are expected (e.g., 6 keV). If such a calibration or correction DAC is provided, it is then advantageous to design the global DAC and the correction DAC separately due to the aforementioned different resolutions. The global DAC may then be applied with a rather lower resolution (e.g., 2 keV/bit) that generates a voltage that is applied on each pixel element of the detector module or for all the detector modules in a detector and on which a pixel by pixel corrected voltage is superimposed pixel by pixel via a higher resolution correction DAC (e.g., 0.1 keV/bit or 0.5 keV/bit). If a plurality of threshold values and counters are provided per pixel element (e.g., spectral imaging), then a plurality of global DACs are necessary. It may be advantageous to provide a calibration or correction DAC for each discriminator in case, for example, the circuit works in a non linear manner.

FIG. 6 shows a diagram for an entire array of counting pixel elements 12 (e.g., 100×100 pixel elements each of 180 μm). In this example, the size of the array would be 1.8×1.8 cm². For large scale X-ray detectors (e.g., 20×30 cm²), a plurality of detector modules 35 are combined (e.g., around 11×17 modules would produce this area) and connected via shared peripheral electronics. For the connection between the ASIC and the peripheral electronics, through silicon via (TSV) technology, for example, is used to provide quadrilateral mounting of the modules side by side.

In the case of counting and energy discriminating X-ray detectors, two or more (e.g., four, as shown in FIG. 7), different threshold values are inserted per pixel by four pairs including a DAC 32 and discriminator 31. The level of the charge pulse, corresponding with the pre-defined threshold values (e.g., discriminator threshold values), is classified into one or a plurality of the digital memory units 33 (e.g., counters). The X-ray quanta counted in a specific energy range may then be obtained by subtracting the counter contents from two corresponding counters. The discriminators 31 may be adjusted, for example, with the aid of digital to analog converters for the entire detector module or pixel by pixel within set limits or ranges. The counter contents of the pixel elements 12 are read out in succession in a modular manner via a corresponding readout unit.

An increase in the spectral resolution by adding further threshold values through additional discriminators and a corresponding DAC or memory unit is accompanied by increased space requirements on the ASIC, such that a random energy discrimination may not be possible at the present time for reasons of space.

It would be possible to reduce the size of the structures that are arranged on the ASIC, for example, by moving from the 180 nm technology to a 130 nm or 90 nm technology or even smaller. As a result thereof, the space requirement for the electronics components on the ASIC would be reduced to implement an energy threshold, so that more energy thresholds altogether may be achieved on the ASIC. However, this procedure would provide a large technological advance, which with only low production runs, may be cost intensive and therefore unprofitable. In medical imaging, the reduction in the sizes of the structures on the ASIC would not result in any reduction in the size of the ASIC itself or of the production costs since the detector area and hence the size of the ASIC are to be retained.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a method for receiving energy selective image data using a counting X-ray detector. The method delivers a high spectral resolution while having a low number of discriminators and DACs on the ASIC. Embodiments also provide a counting, digital X-ray detector suitable for carrying out the method, and an appropriate X-ray system that is suitable for this purpose.

Embodiment further provide a method for receiving energy selective image data relating to an examination object using a counting, digital X-ray detector.

Features, advantages, or alternative embodiments disclosed herein may be applied to the other subjects, and vice versa. In other words, the method may also be further developed with features that are described in connection with an apparatus. The corresponding functional features of the method are further developed by corresponding substantive modules or units.

Embodiments are based on the consideration that a fine spectral resolution in X-ray imaging may be achieved without an additional space requirement on the ASIC of an X-ray detector by subdividing a time interval during which X-rays are applied to an examination object into sub-time intervals, and having the X-ray detector measure the incident X-rays in each sub-time interval in different spectral regions. According to an embodiment, the spectral resolution may be increased as desired.

A method according to an embodiment is provided for receiving energy selective image data relating to an examination object using a counting, digital X-ray detector of an X-ray system. The X-ray detector includes an X-ray converter for direct or indirect conversion of X-rays into an electrical signal, and a matrix having a plurality of counting pixel elements. For each pixel element, at least one modifiable threshold value, above which each incoming signal is counted by a memory unit, may be applied. The method includes the following:

application of X-rays during at least one time interval including a plurality of sub-time intervals;

setting of a first threshold value in the X-ray detector for a first sub-time interval;

conversion of X-ray quanta into count signals while the first threshold value is applied and storage of the count signals in the X-ray detector;

setting of at least one second threshold value in the X-ray detector for at least one respective second sub-time interval;

conversion of X-ray quanta into count signals while the second threshold value is applied and storage of the count signals in the X-ray detector;

readout of the image data from the X-ray detector; and display or storage of the image data.

Consequently, in an embodiment, within a time interval, in which an examination subject is examined using X-rays, a plurality of (e.g., at least two) image data sets are generated. The image data sets differ with respect to the quantum energy of the incident X-rays that is taken into consideration. The differentiation is achieved using at least two different threshold values. In an embodiment, a plurality of energy selective partial images are generated for each time interval. An X-ray detector generates energy selective partial images not simultaneously but in succession, in each case within a sub-time interval. In this way, fewer electronics components may be used on the ASIC of the X-ray detector. Using an X-ray detector that, for example, may only include a DAC and a discriminator, the measurement of various X-ray spectra may be carried out in quick succession. The same threshold value or values may be applied or set for a sub-time interval on all the pixel elements. Global threshold values may be used for the entirety of the X-ray detector. Thus, a modifiable, global threshold value may be set, using, for example, one or a plurality of global DACs for all the pixel elements, for the pixel elements in one module, or for a plurality of pixel elements in the X-ray detector. The X-rays applied may be continuous X-rays lasting over a plurality of time intervals, or pulsed X-rays. Then, the sub-time intervals are in a time interval within an X-ray pulse or are synchronized therewith. Accordingly, embodiments may be extended to any number of time intervals. The various threshold values are random and may vary from case to case in an application specific manner. The determination of the threshold values may be based, for example, on data relating to the X-ray system (e.g., to the type of X-ray image and/or to the properties of the X-ray detector and/or the properties of the X-ray spectrum of the X-rays and/or the properties of the examination object). The X-ray spectrum may be influenced, for example, by the tube voltage or the filtering. The examination object may likewise vary considerably with respect to properties. For example, the determination of the threshold values may be based on one or a plurality of the following data: data relating to the tube current of an X-ray tube and/or the tube voltage of the X-ray tube and/or a degree of hardening of the X-ray beam and/or an angulation or geometry of a receiving system and/or a filtering of the X-rays and/or a water equivalent of the examination object and/or a material property (e.g., die K edge) of the X-ray converter and/or a material property (e.g., the K edge) of the examination object. The threshold values may be determined automatically, with the determination being based on inputs by a user or a physician, for example. Alternatively, the threshold values may be predetermined directly by the user. The threshold values and likewise the lengths of the sub-time intervals may be firmly predefined in the context of an organ program for an X-ray system, and/or a specific type of examination may be firmly predefined, such that the threshold values may subsequently only need to be adjusted by an expert. The energy selective image data generated within a time interval that has been recorded using a different threshold value in each case may be subjected retrospectively to an image processing and/or image correction procedure. For example, the image data acquired within a time interval may be used to generate a monochrome X-ray image for the time interval observed at a desired X-ray quantum energy or, depending on the application or desired image impression required, a weighted total image using the known method of material splitting. The image processing or image correction ensues, for example, in a computation unit of the X-ray system. The image data is read out from the X-ray detector. The readout may ensue in a concerted procedure for all the pixel elements after expiry of a time interval. Alternatively, the readout from the X-ray detector may also ensue while further image data is still being acquired.

The lengths of the time intervals are application specific. Certain time intervals include a length of, for example, 3 ms to 200 ms. In angiography, for example, time intervals of around 5 ms to 30 ms are used in fluoroscopy (at low doses). For digital subtraction angiography image series (at higher X-ray doses), time intervals with a length of around 30 ms to 200 ms are used. In radiography, time intervals of up to 200 ms may occur. However, time intervals with lengths outside the stated range may also be used. For example, the time interval lengths for computer tomography are considerably shorter.

With pulsed X-rays, as are widely used nowadays, for example, pulses 30 ms long are arranged with intervals between the pulses of, for example, 20 ms, in which no X-rays are applied. This time may be used, for example, to read out the image data from the X-ray detector. With continuous X-rays, the readout from the X-ray detector is to ensue at the same time as the data acquisition. For this, purpose, shadow registers may be used.

The procedure described only prescribes a fixed sequence or series of acts insofar as is necessary. For example, the first sub-time interval is before the at least one second sub-time interval, and the count content acquired with respect to the first sub-time interval is to be stored before the acquisition of the count content with respect to the at least one second sub-time interval. The sequence of acts in the context of the method according to an embodiment is variable, however, or not fixed by the embodiments. For example, acts may also ensue simultaneously. In a variant of the method according to an embodiment, the lengths of the sub-time intervals are determined based on the mean count rates to be expected with regard to the respective threshold values during the sub-time intervals. The shape of the spectrum of the X-rays incident on the X-ray detector essentially depends on the properties of the X-ray source, the type of examination, the body region that is to be examined, hardening effects and suchlike. The shapes of the spectrum of the X-rays incident is a distribution function with any shape. In other words, the beam intensity is dependent on the quantum energy, such that the image data acquired in various sub-time intervals for different threshold values has photon statistics that differ from one another. The X-ray images pertaining thereto accordingly show varying degrees of noise. Photon statistics for the individual images may be harmonized by adjusting the length of the sub-time intervals, standardized to the length of the time interval and the total count rate, taking into account the expected count rate at the various threshold values in the sub-time intervals. Sub-intervals at threshold values with a low mean expected count rate accordingly last longer, while sub-time intervals at threshold values with a high mean expected count rate are accordingly shorter. The harmonization of the photon statistics makes post and further processing of the energy selective images considerably easier. The prerequisite for this procedure is the fact that X-rays are applied during the entire time interval. The mean expected count rates may ensue, for example, from previous test measurements with the X-ray spectrum desired for the X-ray imaging, with a defined X-ray flux (kVp, mAs) and/or a defined pre filtering, may be retrievably stored in tables, or may be determined by simulation. The counter depth (e.g., number of bits) is to be of sufficient size to be able to detect all applications (e.g., including the applications with high X-ray fluxes and long sub-time intervals). The X-ray system may calculate the lengths of the sub-time intervals automatically or in response to commands from a user or may access stored values therefor. Alternatively, the length of the sub-time intervals may be fixed directly by a user.

The lengths of the sub-time intervals may in each case be based on the inverse of the mean expected count rates for the respective threshold values during the sub-time intervals. In this way, approximately identical photon statistics are achieved in the X-ray images within a time interval.

In an embodiment, the lengths of the sub-time intervals are identical. In other words, the sub-time intervals are divided equidistantly across the time interval. In this embodiment, comparable noise properties are only achieved when the spectrum of incident X-rays approximately corresponds to a rectangular function, which may not be the case. For example, the time interval is 30 ms, and the time interval is subdivided in view of the application into three sub-time intervals of equal length of 10 ms. The at least one modifiable threshold value may be retrievably stored in each pixel element before X-rays are applied. For example, the previously stored threshold value may be a global threshold value that is set for all the pixel elements in the X-ray detector in the transition to a subsequent sub-time interval. In the transition from one sub-time interval to the next sub-time interval, the prior storage of the threshold value in each pixel element allows a rapid switchover from one threshold value to the next that reduces data transfer and the resulting loss of time. In this way, an approximately loss free X-ray acquisition and hence optimum utilization of the applied X-rays, which occurs continuously across the entire time interval, is achieved. In one embodiment, the switchover of the threshold value occurs instantaneously.

In a further embodiment, storage of the count signals in the X-ray detector includes transmitting, from the memory unit that is performing the count during the sub-time interval, count signals relating to each pixel element that have been acquired for each sub-time interval into a further memory unit, a register, for example, directly after the expiry of the sub-time interval. The counting memory unit may be a counter that evaluates each pulse above the threshold value as an event and counts the pulse accordingly. Each pixel element is connected to such a counting memory unit. Each pixel element may include an individual, counting memory unit. For each sub-time interval, the count content from the counting memory unit is to be deleted or put back to zero, so that the counting memory unit may begin the counting of events or X-ray quanta again for each sub-time interval. For this purpose, the count value or count content of the counter from the previous sub-time interval is transmitted into the further memory unit that may likewise be assigned to each pixel element individually. The transmission from the counting memory unit to the further memory unit is considerably faster than the transmission to the peripheral electronics, where the count values are further processed, such that, after a short readout phase of, for example, 100 ns, the counting memory unit is available again for recording events. The transmission to the further memory unit ensues, for example, simultaneously for all the pixel elements and is consequently very fast. This has the advantage that hardly any image data losses occur since approximately the entirety of the incident X-rays within a time interval are detected.

If the further memory unit is configured to store only the count value for one sub-time interval, the storage of the count signals in the X-ray detector may include the transmission, from the further memory unit, of count signals relating to each pixel element that have been acquired for each sub-time interval to the peripheral electronics of the X-ray detector within the subsequent sub-time interval. The transmission time is not to exceed the length of the subsequent sub-time interval since, after that, the further memory unit again is to be receive capable (e.g., free for the count value of this sub-time interval). With regard to the subsequent sub-time interval, the readout may last for any length of time, however. If the length of the sub-time intervals is 10 ms, the data transfer from the further memory unit is to have taken place within 10 ms. Once again, the readout time is defined, however, by the shortest sub-time intervals that are practically possible and accordingly is to be specified on the detector (e.g., readout clock frequency). If the shortest time interval is, for example, 1 ms long, then the transmission of the count values for all the pixel elements in an ASIC to the peripherals is to last for a maximum of 1 ms. In a simplest form, this readout is configured to be sequential (e.g., one pixel element in the ASIC is read out after the other). However, the readout of a plurality of pixel elements in an ASIC may also ensue in parallel (e.g., simultaneously). In general, if there is more than one counter per pixel element, a further memory unit is to be available for each counter, and the readout of all the further memory units for all the pixel elements in the ASIC is to ensue within the 1 ms given as an example. The X-ray detector may include a plurality of ASICs. In one embodiment, the readout of the ASICs likewise ensues in parallel.

In an alternative embodiment, pixel by pixel count values for a plurality of (e.g., at least two) sub-time intervals are stored in parallel. For example, the count values for all the sub-time intervals in a time interval are stored before a transmission to the peripherals ensues. This has advantages when, for example, a calculation or further processing of the acquired image data is already intended to ensue in a pixel element or before transmission to the peripherals. This saves additional data transfer and transmission time, since in this way, only one readout process is to be carried out per time interval.

In an embodiment, a setting of a threshold value in the X-ray detector for a sub-time interval includes an adjustment of the threshold value that is specific to each pixel element. The adjustment, in addition to the setting of a global threshold value that is identical for each pixel element, makes individual corrections of the global threshold value for each pixel element. The corrections are necessary, for example, if as mentioned at the beginning, there are fluctuations of pixel element amplifiers, imperfections in the detector material, or material related non-homogeneities from pixel to pixel. While the global threshold value is, for example, set up in analog form on the discriminator of a pixel element or is set up via a DAC, a corrected value specific to the individual pixel may be available in digital form in the pixel element in, for example, an on pixel memory provided for this purpose, and the global threshold value may be adjusted using a correcting DAC. For this purpose, a corrected voltage specific to the individual pixel is superimposed on the global threshold value voltage on the discriminator.

In an embodiment, a setting of a threshold value includes setting a lower energy threshold, above which the incoming signal is counted, and an upper energy threshold, below which the incoming signal is counted. The embodiment allows for two kinds of options. First, a unilateral threshold value may be set, referred to as a unilateral discriminator. A count is carried out when the signal exceeds a set threshold value. Alternatively, a window discriminator is applied, with a lower and an upper energy threshold. In this case, a count is only carried out when the reading falls below the upper threshold and falls above the lower threshold. A window discriminator is also referred to as energy binning. In order to obtain corresponding count values for energy bins for the first alternative in the second option, the count values for the relevant sub-time intervals may be subtracted from the corresponding threshold values.

In an embodiment, at least two different modifiable threshold values may be applied at the same time for each pixel element. This procedure increases the spectral resolution of the X-ray image since at least two threshold values may be measured in parallel for one sub-time interval. This variant may be set up, for example, with two or more global DACs for all the pixel elements, for those in one module, or for any plurality of pixel elements in the X-ray detector with in each case at least two modifiable threshold values per sub-time interval.

An embodiment relates to a counting, digital X-ray detector in an X-ray system for receiving energy-selective image data. The counting, digital X-ray includes an X-ray converter for direct or indirect conversion of X-rays into an electrical signal, and a matrix including a plurality of counting pixel elements. For each pixel element, at least one modifiable threshold value, above which each incoming signal is counted by a memory unit, may be applied. The X-ray detector may be equipped to carry out the method according to an embodiment.

An embodiment relates to a counting, digital X-ray detector including at least one discriminator. The X-ray detector is equipped to apply the modifiable threshold value within a time interval that includes a plurality of sub-time intervals such that, in a first sub-time interval, a first threshold value is applied on at least one pixel element, and in at least one second sub-time interval, a second threshold value is applied on the at least one pixel element. This X-ray detector is consequently equipped to generate energy selective image data within a time interval. The energy selective image data is generated consecutively and in each case within a sub-time interval. The DAC may be a global DAC, via which the same modifiable threshold value is applied for all the sub-time intervals on all the pixel elements simultaneously. Alternatively, the DAC may apply only pixels for one module or only one single pixel element with the modifiable threshold value. Consequently, a plurality of DACs may be provided in the X-ray detector. The plurality of DACs apply, for each sub-time interval, an identical global threshold value for all the pixel elements.

According to a further embodiment, each pixel element in the counting, digital X-ray detector includes a memory unit for storing the at least one modifiable threshold value. In other words, each pixel element includes an on-pixel memory for the various modifiable threshold values. In this way, for the switchover from one threshold value for a first sub-time interval to the threshold value for a second sub-time interval, the method may be sped up since data transfer and hence the accompanying loss of time are minimized.

In an embodiment, the counting, digital X-ray detector includes, alongside the counting memory unit, a further memory unit for intermediate storage of the count signals. The further memory unit may be configured as a register, for example. Instead of a register, a second, counting memory unit that is always operated in alternation with the first counting memory unit may be provided; while one counts, the other is read off into the peripherals, and vice versa. In a further variant, the further memory unit is equipped to store a plurality (e.g., at least two or all) of the sub-time intervals in a time interval in parallel before the sub-time intervals are read out. The further memory unit may be configured to be specific to an individual pixel and store only count values for one pixel element. Alternatively, the further memory unit may also be equipped to store the count values relating to a plurality of pixel elements. In other words, in this case, a plurality of counters have a shared further memory unit.

In order to increase the spectral resolution of the measurement within the time interval, in an embodiment, the counting, digital X-ray detector is equipped with at least two DACs for the simultaneous setting of at least two modifiable threshold values. Each DAC serves for the simultaneous setting of one of the at least two different, modifiable threshold values.

An embodiment relates to an X-ray system for X-ray imaging to implement a method. The X-ray system includes:
- an X-ray tube to emit X-rays that irradiate an examination object during at least one time interval that includes a plurality of sub-time intervals;
- a counting, digital X-ray detector including an X-ray converter for direct or indirect conversion of X-rays into an electrical signal and a matrix having a plurality of counting pixel elements, where for each pixel element, at least one modifiable threshold value may be applied in each case for the duration of a sub-time interval, above which value each incoming signal is counted using a memory unit;
- a system control to control the X-ray system;
- a computation unit to determine the length of the sub-time intervals; and
- an imaging system to process and display the image data.

The computation unit takes into account (e.g., in the determination of the length of the sub-time intervals) the mean count rate that is to be expected for a sub-time interval and the respective threshold value. The computation unit may additionally be equipped to determine the threshold values or process inputs relating thereto by a user to determine the threshold values.

In an embodiment, the X-ray system may be configured as a computer tomograph, angiography system, mobile or robot assisted C-arm system, a projection radiography system or suchlike.

The invention is not restricted by this description to the embodiments disclosed.

DETAILED DESCRIPTION

Figure 1:
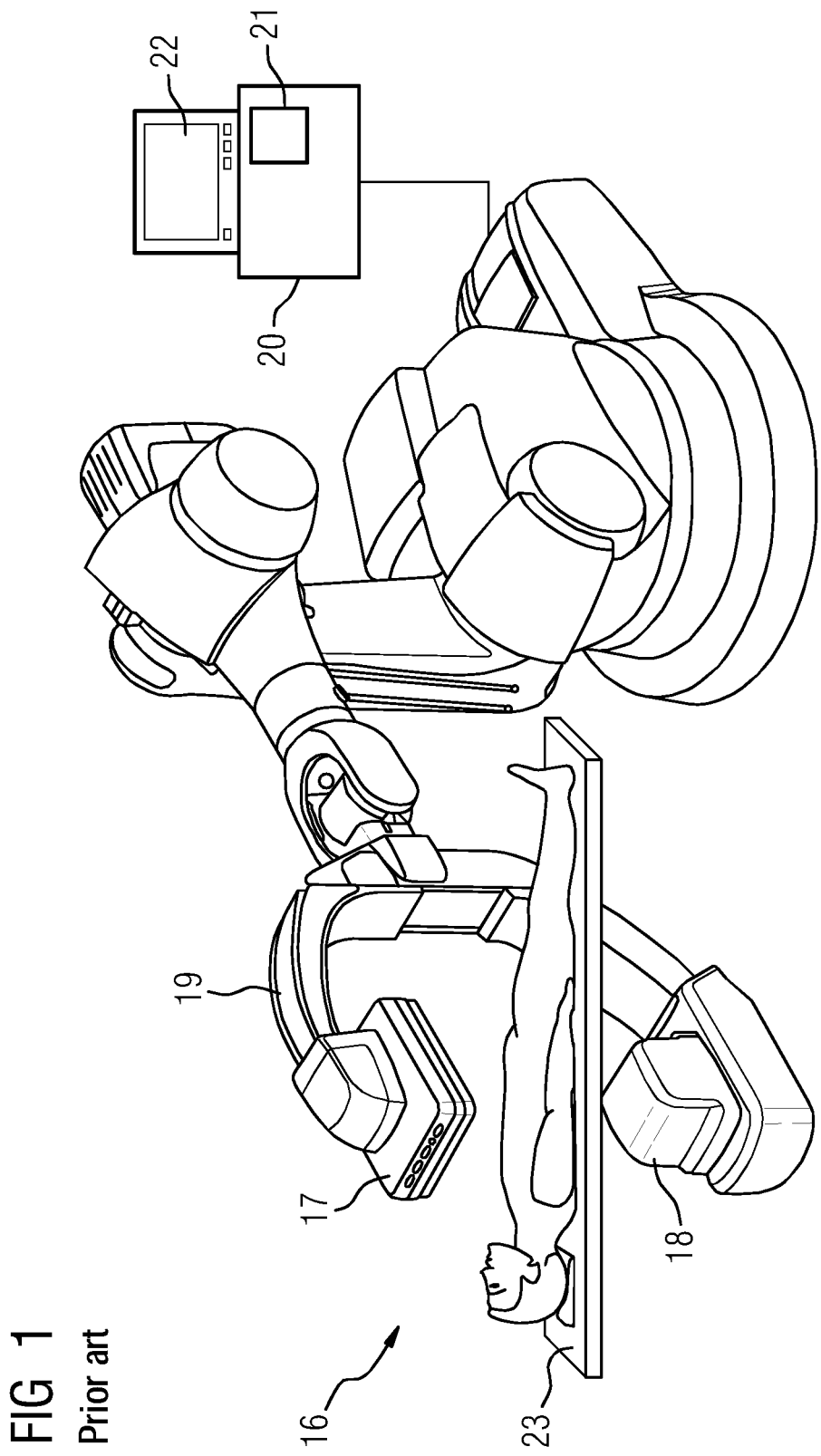
FIG. 1 depicts an example X-ray system used in interventional procedures.
Figure 2:
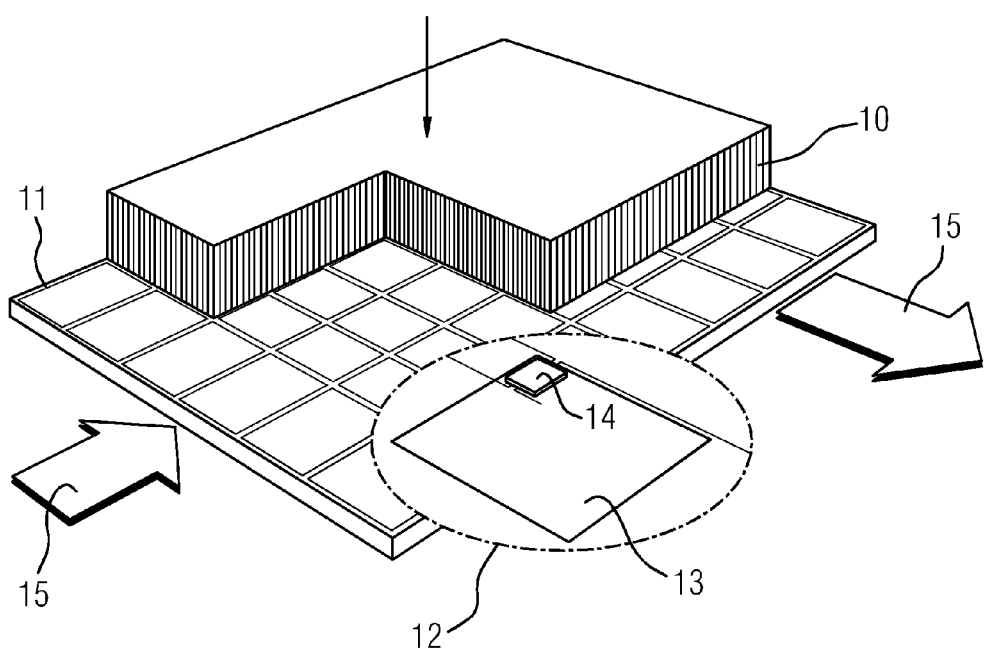
FIG. 2 depicts an example X-ray detector with a scintilator.
Figure 3:
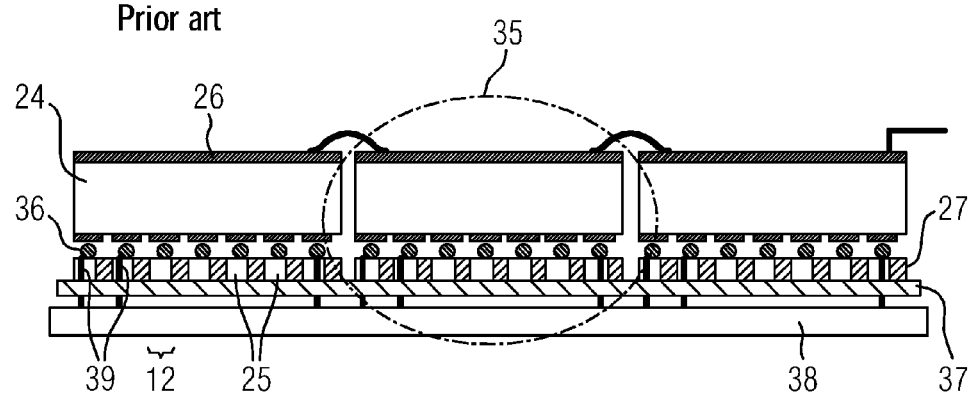
FIG. 3 depicts a cross section through a segment of an example X-ray detector with a plurality of detector modules.
Figure 4:
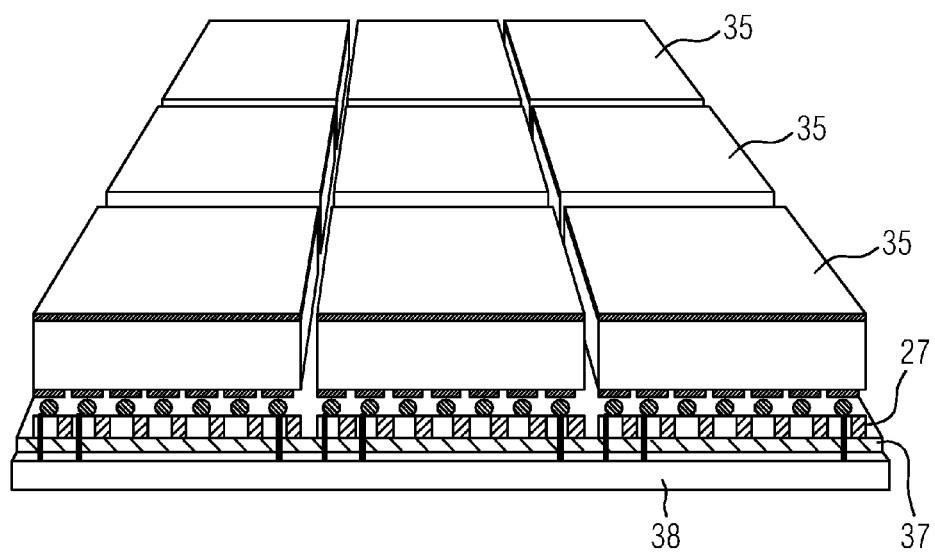
FIG. 4 depicts a perspective top view of a segment of an example X-ray detector with a plurality of detector modules.
Figure 5:
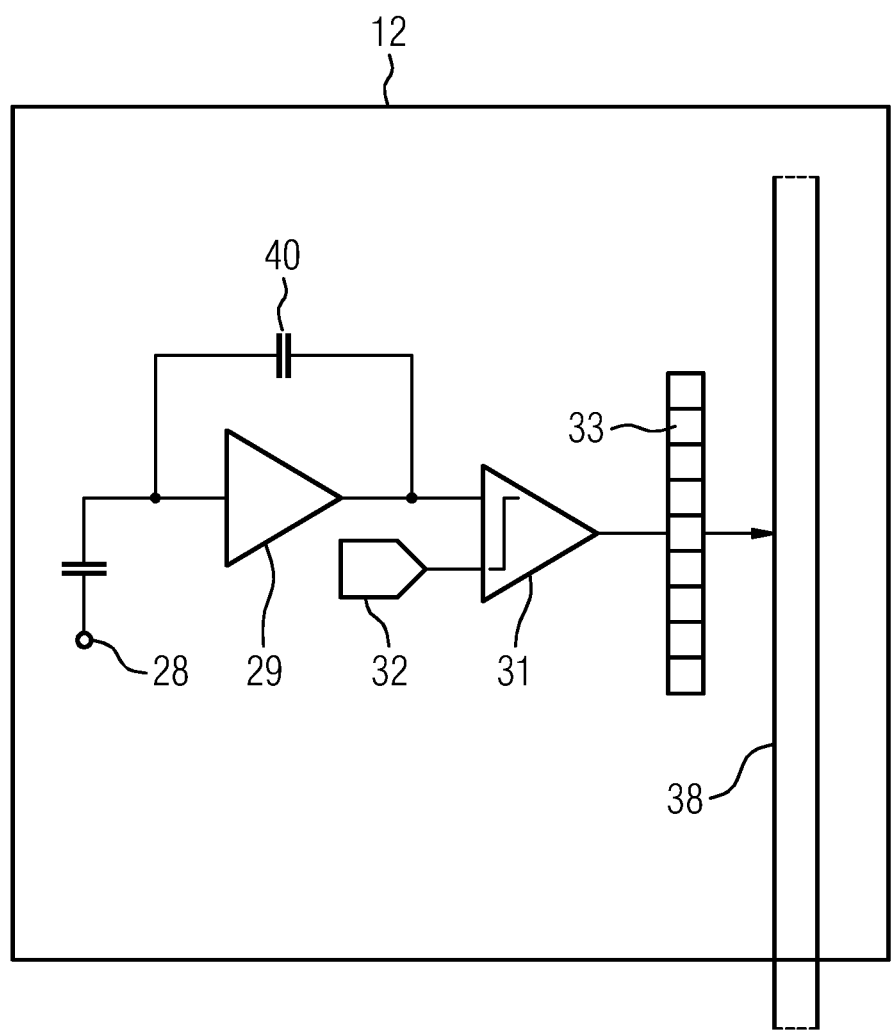
FIG. 5 depicts an example of the central functional elements of a counting pixel element of an X-ray detector.
Figure 6:
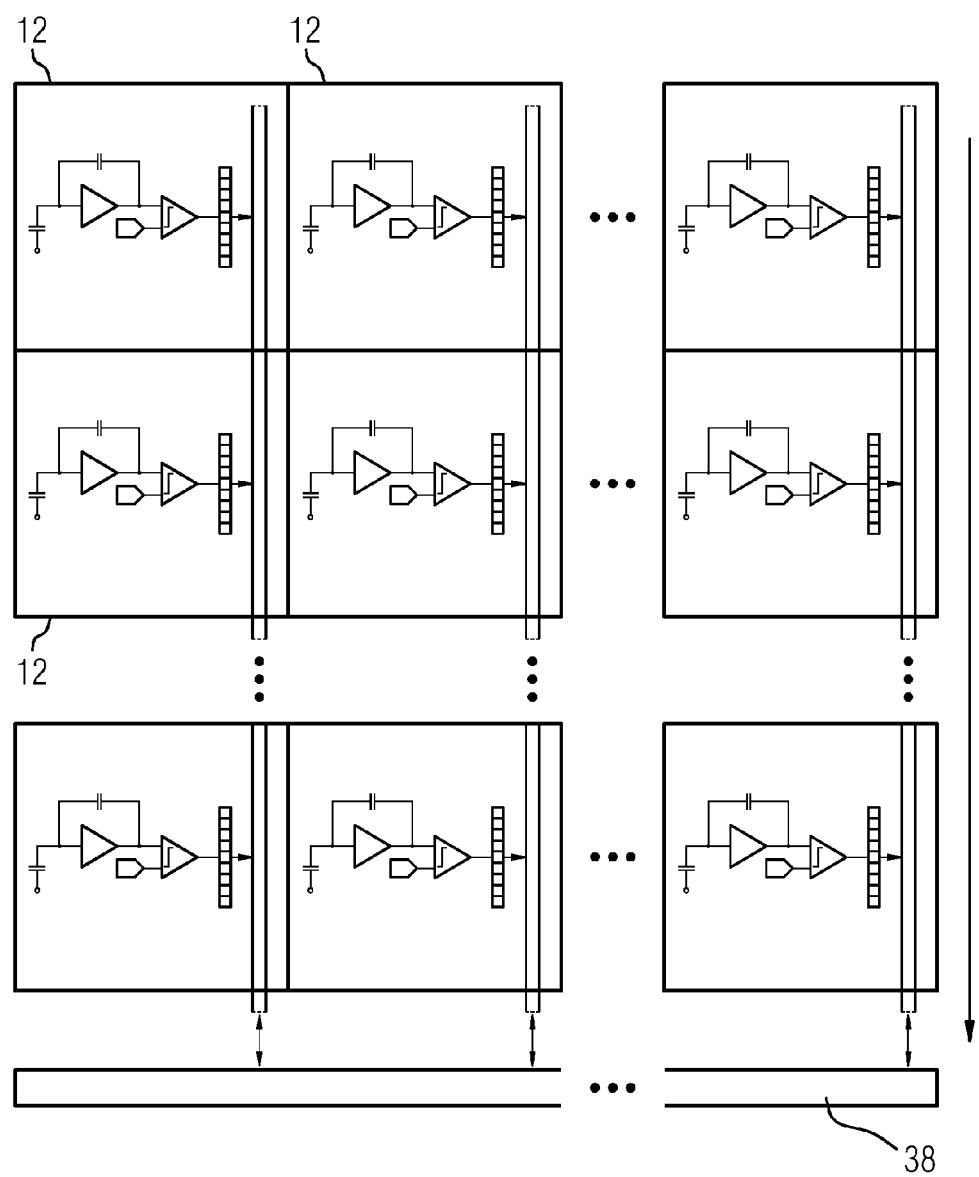
FIG. 6 depicts an example matrix of counting pixel elements in an X-ray detector with control and readout logic.
Figure 7:
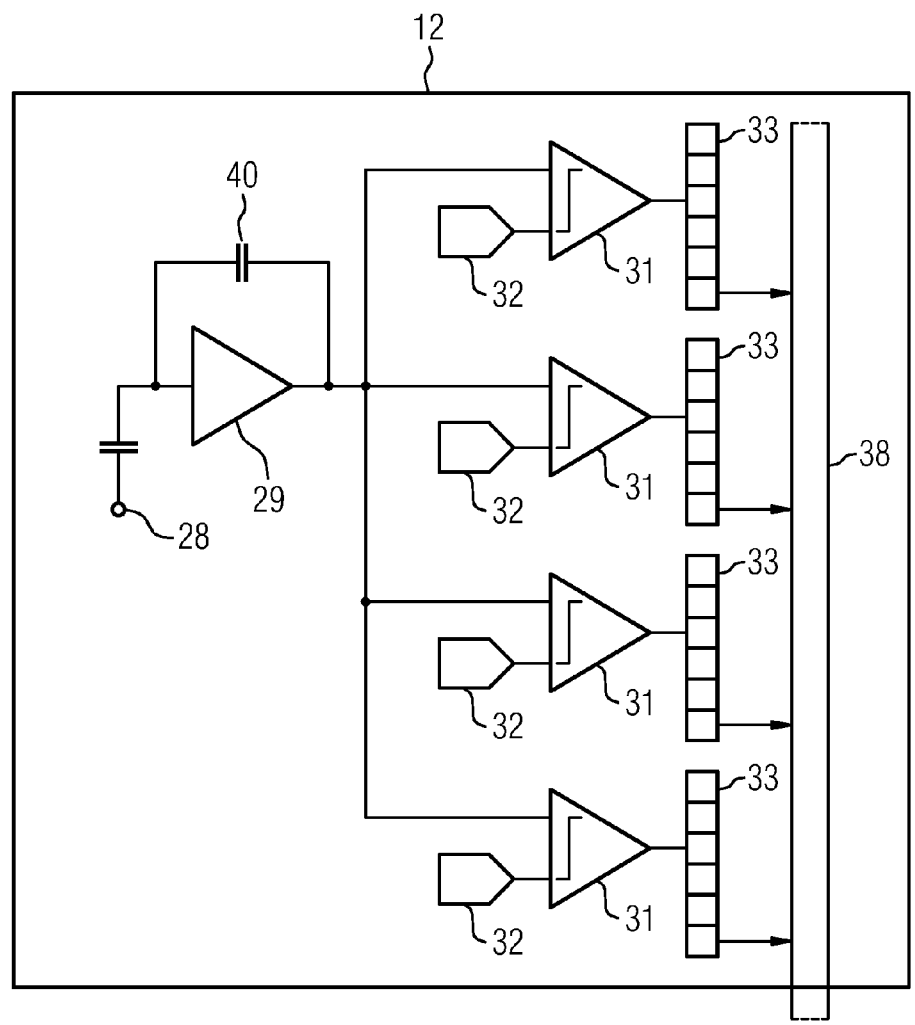
FIG. 7 depicts an example of the central functional elements of a pixel element in a counting, energy discriminating X-ray detector.
Figure 8:
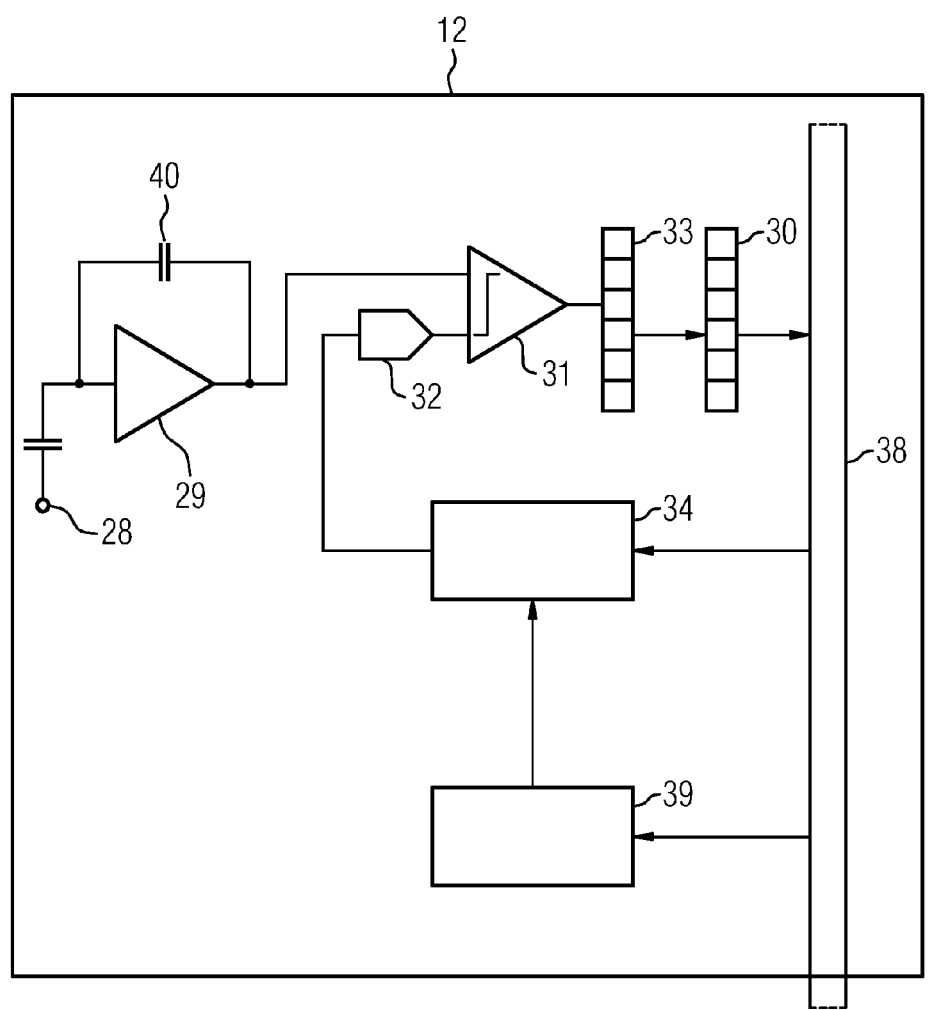
FIG. 8 depicts the central functional elements of a pixel element of an X-ray detector according to an embodiment.

FIG. 8 depicts an illustration of the central functional elements of a pixel element 12 of an X-ray detector according to an embodiment. In this embodiment, each pixel element 12 in the X-ray detector is designed as shown. In addition to a pre-amplifier 29, each pixel element 12 includes a discriminator 31 and an assigned memory unit 33 in the form of a counter. The threshold values (k) with k=1, K are digitally coded in this example, and before the X-ray image is received, the threshold values are available in a memory unit 34 provided for this purpose on the pixel element 12 in the form of a threshold value memory. The threshold values (k) are global threshold values (e.g., for each sub-time interval, the same threshold value (k) is applied on each pixel element 12). For the $(k)^{th}$ sub-time interval, a corresponding threshold value (k) is applied via the DAC 32 on the discriminator 31. Within the $(k)^{th}$ sub-time interval, incoming pulses that are above the threshold value voltage on the discriminator 31 are counted. At the end of the $(k)^{th}$ sub-time interval, the count content C(k) of the counter 33 is recorded in the further memory unit 30 in the form of a register, and the count content of the counter 33 is put back. A clock 39 essentially records the expiry of the $(k)^{th}$ sub-time interval simultaneously and triggers the threshold value memory 34 to transfer the threshold value (k+1) to the DAC 32, which is applied for the duration of the $(k+1)^{th}$ sub-time interval at a corresponding threshold value voltage on the discriminator 31. During the duration of the $(k+1)^{th}$ sub-time interval, the count content C(k) of the register 33 is transmitted to the peripherals 38, which include control and readout electronics, for further processing. The threshold value memory 34 is in a communication connection with the peripherals 38 in order, for example, to request and/or download desired threshold values (k) for receiving an X-ray image. In this embodiment, the request occurs before receiving the X-ray image. The clock 39 is likewise in a communication connection with the peripherals 38 in order, for example, to request and/or download the number and length Tk of the sub-time intervals. This may likewise occur before or on time during the receiving of the X-ray image. Both the threshold values and the lengths of the sub-time intervals may be made available to the peripherals 38 of the X-ray detector by a computation unit and/or a control unit of the relevant X-ray system. Alternatively, the threshold values may also be made available by a user via the input interface of the X-ray system.

Figure 9:
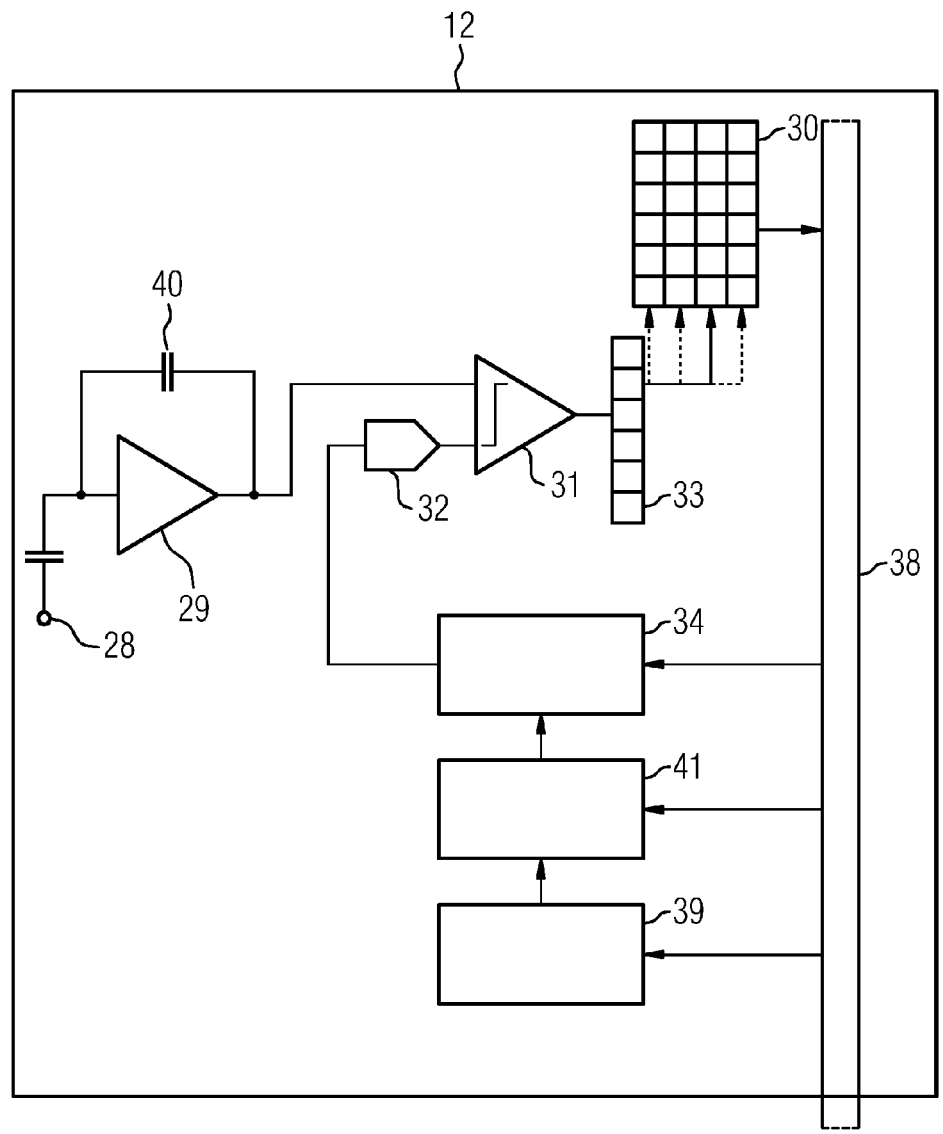
FIG. 9 depicts the central functional elements of a pixel element of an X-ray detector according to an embodiment.

FIG. 9 depicts an illustration of the central functional elements of a pixel element 12 of an X-ray detector according to a different embodiment. In this embodiment, each pixel element 12 in the X-ray detector is configured as shown. The pixel element shown in FIG. 9 differs from that shown in FIG. 8 by a further memory unit 41 in the form of a memory for pixel-specific corrected values. In order to obtain these, the corrected value memory 41 is in a data connection with the periphery 38. The pixel-specific corrected values may emerge, for example, from calibration procedures carried out before the receipt of an X-ray image. The corrected values may, for example, be subjected to an update before the receipt of each new X-ray image. The pixel element 12 shown includes a further memory unit 30 in the form of a register to read out the counter 33. The register 33 is configured to store all the count contents C(k) of the pixel element 12 for the duration of an entire time interval T before this is read off into the peripherals 38.

Figure 10:
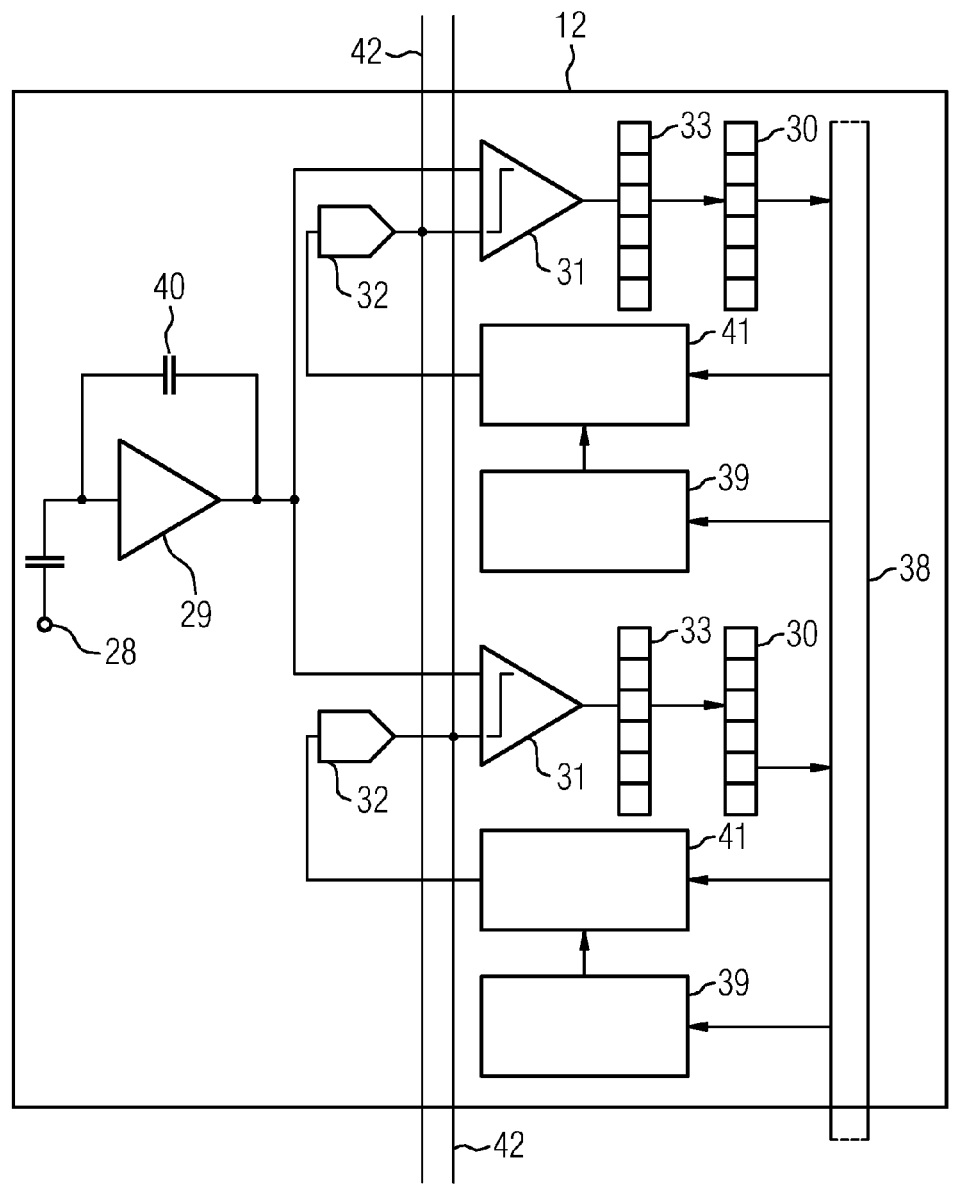
FIG. 10 depicts the central functional elements of a pixel element of an X-ray detector according to an embodiment.

FIG. 10 depicts an illustration of the central functional elements of a pixel element 12 of an X-ray detector according to a further embodiment. In this embodiment, each pixel element 12 in the X-ray detector is configured as shown. Hereinafter, only the differences from the previous embodiments of FIGS. 8 and 9 are described. According to this example, the pixel element 12 includes two discriminators 31, two DACs 32, two counters 33, and two registers 30. Doubling the structures provides that, for example, a doubling of the spectral resolution may be achieved by setting, for each sub-time interval, modifiable threshold values (k) that differ from each other on the two discriminators 31. The sub-time intervals in the first and the second discriminator 31 are not intended to differ from each other in this embodiment. Each of the two counters 33 and each of the two registers 30 is identical to the counter 33 or register 30 that are shown in FIG. 8 and is operated as already disclosed with reference to FIG. 8. The two global threshold values that also differ from each other are provided in analog form, each via a corresponding connection 42 with two global DACs (not shown), are applied on the discriminators 31, and are not generated for the first time locally via a DAC 32. However, this example also includes two DACs 32. The two DACs generate corrected voltages from pixel specific corrected values for the respective global threshold values stored in two corrected value memories 41 in order to compensate for pixel to pixel fluctuations.

Any combinations and sub-combinations may be carried out where technically possible and expedient. Embodiments include: in the case of a unilateral discriminator 31, the register 33 may be configured to store the count contents C(k) of two sub-time intervals, such that a subtraction may ensue to generate an energy bin ΔEk while still in the pixel element 12. Instead of a register 33, a further counter 33 (not shown) may be connected in parallel to the first counter 33; the two counters are connected or connectable both to the discriminator 31 and to the peripherals 38 and are used alternately for counting and for transmitting the current count content C(k) to the peripherals 38. The present concept may also be linked up without difficulty to summation and/or anticoincidence circuits of pixel elements 12 in order to exclude the possibility of double counts or incorrect counts and/or in order to be able to reconstruct energies from a detection event when disseminating the event to a plurality of pixel elements.

Figure 11:
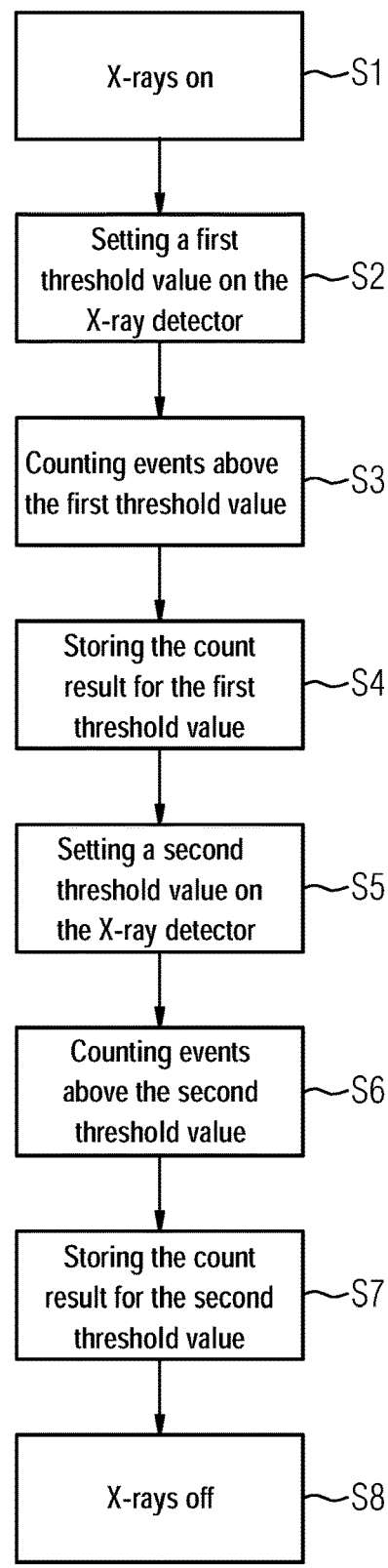
FIG. 11 depicts an example flow diagram according to an embodiment.

FIG. 11 shows a flow chart of a method according to an embodiment. In an act S1, the application of X-rays onto an examination object is started using an X-ray tube, for example. The X-rays are applied continuously for the duration T of a time interval including a plurality of sub-time intervals (e.g., at least two sub-time intervals). In an act S2 that may ensue simultaneously with S1, a first threshold value is applied on an X-ray detector. This threshold value (k) is now applied for the duration Tk of a first sub-time interval. During this first sub-time interval, act S3 ensues (e.g., the counting of events above the threshold value that occur in the X-ray detector within the first sub-time interval). In an act S4, after the expiry of the first sub-time interval, the count result C(k) for the first sub-time interval is stored in the X-ray detector. In an act S5, that may ensue simultaneously with act S4, a second threshold value is applied on the X-ray detector 17 for the duration of the second sub-time interval Tk+1. In an act S6, events that are above the second threshold value (k+1) are counted over the duration of the second sub-time interval Tk+1. The count result C(k+1) for the second sub-time interval is subsequently stored in the X-ray detector in act S7. Directly after the expiry of the second sub-time interval or at any later point in time, the application of X-rays may be terminated according to act S8. Before the X-rays are switched off, further threshold values (e.g., two further threshold values) may be set and measured for both a third and a fourth sub-time interval. The sequence of acts S2 to S4 for the first sub-time interval may be transmitted or inserted for this purpose. The X-rays may be continuous X-rays or pulsed X-rays. In the case of pulsed X-rays, there is a time interval within an X-ray pulse, and the time interval is, for example, of equal length with an X-ray pulse. The method disclosed may also be extended such that, alongside acts S2 to S7, at the same time, at least one further threshold value may be set in each case on the X-ray detector, and events above this may be counted and stored.

The length Tk of the sub-time intervals may emerge, for example, from the equidistant subdivision of the time interval according to the number of sub-time intervals. However, the result thereof may be non-homogeneous photon statistics relating to the count signals received per sub-time interval. As a result of a selection of the (relative) length of the sub-time intervals, these fluctuations may be compensated for.

The length T of a time interval emerges from the total of the lengths Tk of the sub-time intervals at T=ΣTk. A good harmonization of the photon statistics may be achieved, for example, if the length Tk of the sub-time intervals is assumed as a function of the mean expected count rate <Ck> for the $k^{th}$ energy bin ΔEk (k=1,K) according to Tk=f (<Ck>). Here <Ck> is essentially dependent on the energy bin ΔEk observed and also from the spectrum S of the impinging X-rays such that <Ck>=f(ΔEk,S) applies. A particularly good harmonization of the noise characteristics within a time interval T may be achieved if the sub-time interval length Tk is inversely dependent on the mean expected count rate <Ck> according to Tk=T*<C>)/<Ck>, where standardization was carried out to the length of the time interval T and the mean total count rate for all the energy bins <C>. With a count rate moving towards zero in one or a plurality of energy bins, the length of the sub-time interval is restricted.

Figure 12:
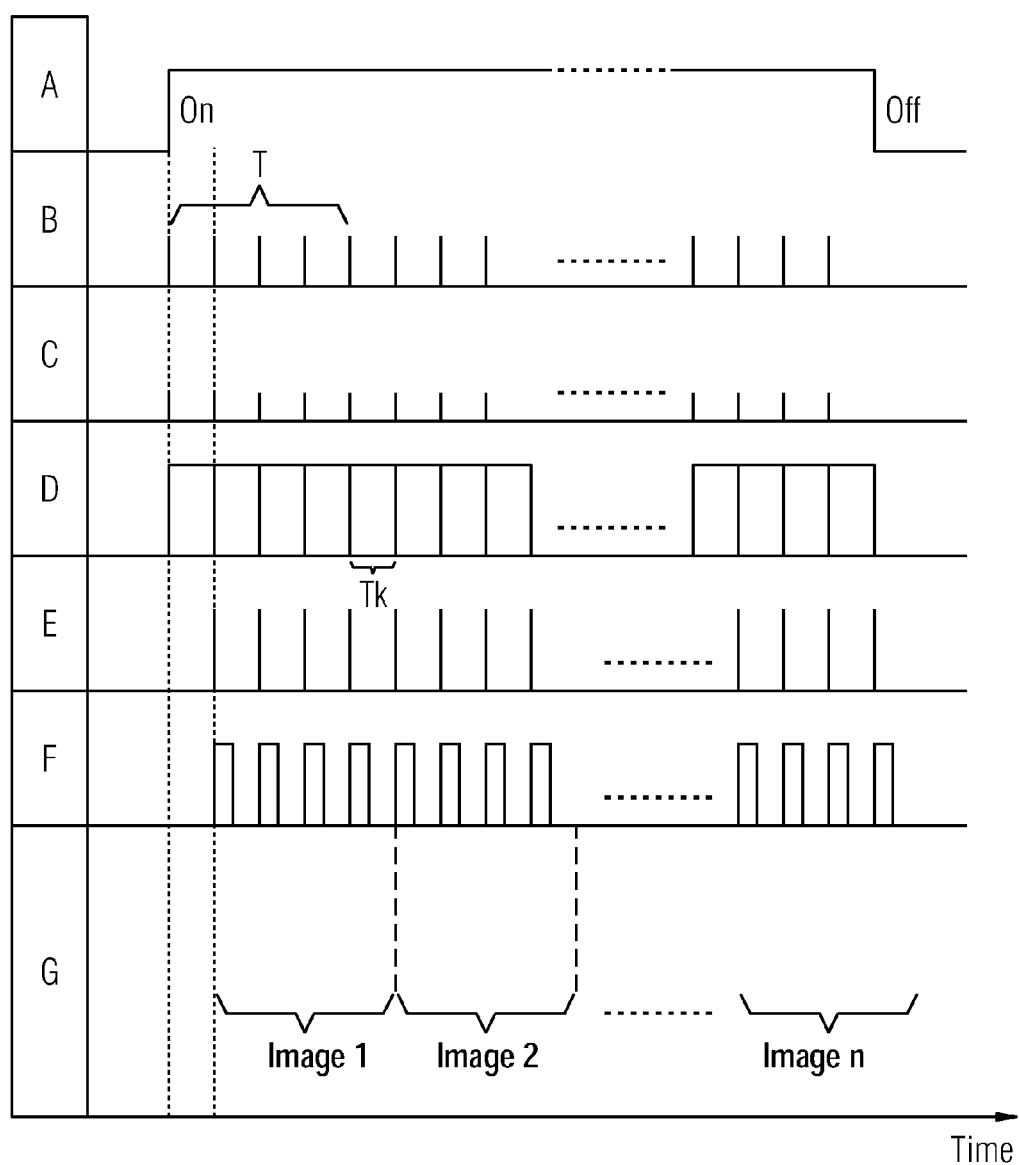
FIG. 12 depicts a time chart of the method according to an embodiment.
Figure 13:
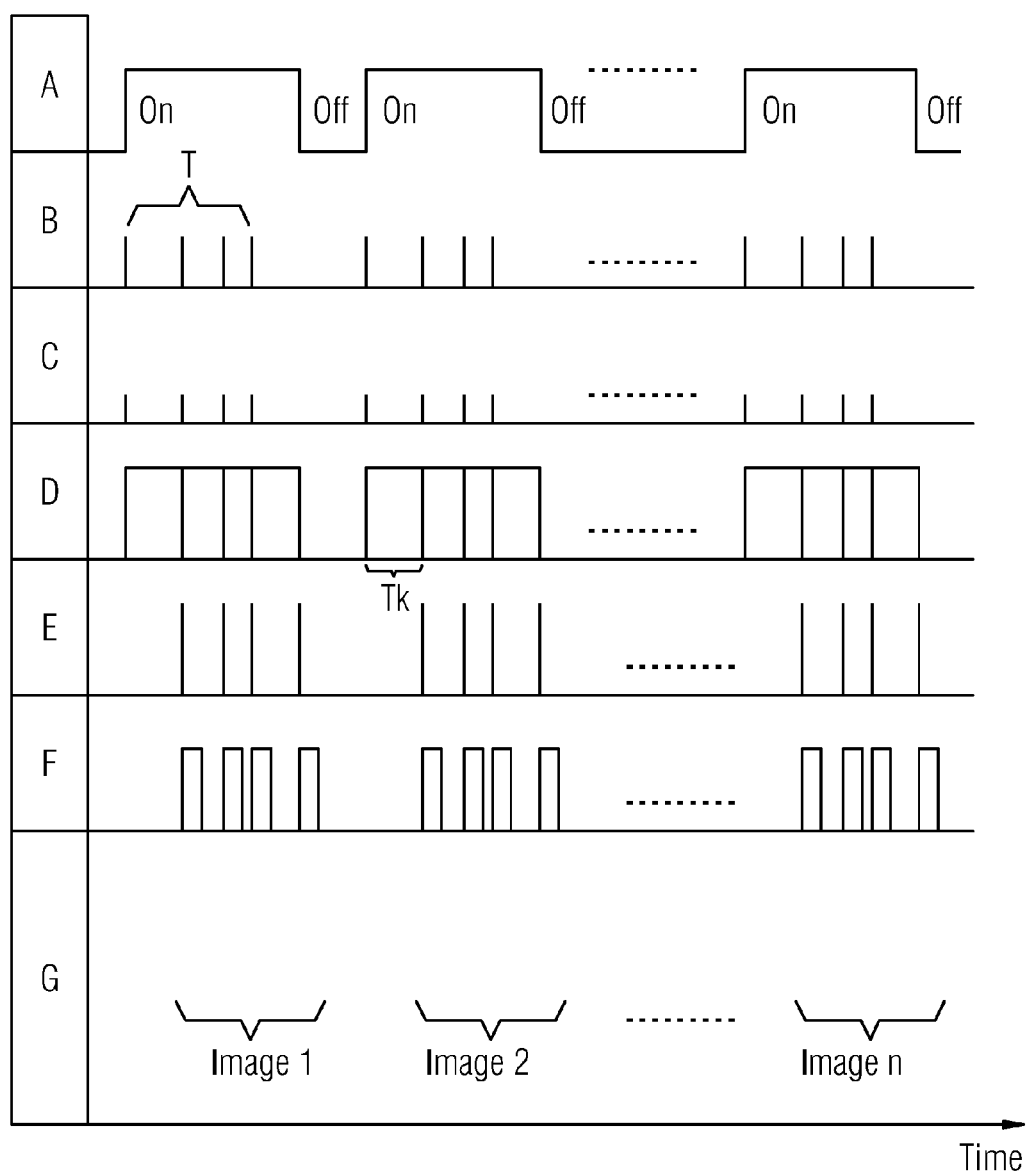
FIG. 13 depicts a time chart of the method according to a further embodiment.

FIG. 12 and FIG. 13 each depict a time graph for the method according to two embodiments, respectively. The time axis runs horizontally from left to right. In lines A to G for both diagrams, respective points of time within the method are marked. Line A represents the application of X-rays. While in FIG. 12, continuous X-rays are shown (a start(ON) and a stop (OFF)), FIG. 13 shows pulsed X-rays that run over time through a plurality of start and stop points, in which the radiation is turned on or off in each case. Line B shows in each case the points in time when global threshold values are applied or set on an X-ray detector. Four threshold values (k) are set in each case; in FIG. 12, the points in time for the four threshold values (k) are spaced apart equidistantly within the time interval for the length T (e.g., all the sub-time intervals have the same length Tk). Alternatively, in FIG. 13, the points in time are distributed non-homogeneously within the time interval (e.g., the sub-time intervals differ in the length Tk). Line C shows the points in time at which pixel specific corrected values relating to the threshold values are applied in order, for example, to compensate for pixel to pixel non-homogeneities. This occurs in each case at the same time as the setting of the global threshold values, or in other words, always at the start of a new sub-time interval. Line D represents the lengths Tk of the respective sub-time interval and consequently indicates the period of time within which signals above the respective threshold value are counted. Line E indicates the points of time at which a transfer of the count results C(k) for a sub-time interval from a counting memory unit 33 in a register 30, for example, ensues together with the resetting of the entry on the counting memory unit 33. This act ensues in each case with the transition from the sub-time interval that has just been observed to the next one. Line F indicates the periods of time in which the count results for sub-time intervals are transmitted to the peripherals 38. In both embodiments, this transmission ensues in each case within the sub-time interval that follows the sub-time interval that has been observed. For example, in situations comparable to the embodiment in FIG. 13 with sub-time intervals of different lengths, it may be provided that the duration of a transfer to the peripherals 38 does not exceed the length Tk of a sub-time interval. As an alternative to a transfer in the consecutive sub-time interval, a transmission may only ensue at the end of a time interval, with the register 30 being configured accordingly. According to line G, the energy discriminating image data acquired as described is subjected to an image processing or image correction procedure. This may include, for example, detector relevant corrections, such as defect or gain correction. Subtractions to energy bins may start right after the receipt of image data for two sub intervals or of two partial images each for one sub-time interval. Such image processing or correction procedures provide a further optimization of the display of the X-ray images, for example, by eliminating noise or artifacts from the image data such that a physician may derive relevant information for diagnosis or therapy from the X-ray images in a simple manner. For example, the energy selective image data acquired within a time interval is assigned to one X-ray image in each case. For example, all the energy selective image data acquired within one time interval is assigned to one X-ray image, for example, using a weighted summation corresponding with a desired image impression (image 1, . . . , image n). Other processing options are likewise possible. Any number of time intervals may be arranged along the timeline, and the method may be carried out repeatedly. In FIG. 13 as a result of the X-rays being pulsed, there are gaps in which no X-ray detection ensues. Storage or transmission procedures are very likely to ensue in these gaps, however. The points of time for the setting of the threshold value, the setting of the corrected value, and the count interval are to be adjusted in this case to the course of the X-ray pulses.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for receiving energy selective image data relating to an examination object by a counting, digital X-ray detector of an X-ray system, wherein the counting, digital X-ray detector comprises an X-ray converter for direct or indirect conversion of X-rays into an electrical signal and a matrix comprising a plurality of pixel elements, wherein for each pixel element of the plurality of pixel elements, at least one threshold value, above which an incoming signal is counted in each case by a memory unit, is applicable, the method comprising:

applying X-rays during at least one time interval that includes a plurality of sub-time intervals;

setting a first threshold value of the at least one threshold value in the counting, digital X-ray detector for a first sub-time interval of the plurality of sub-time intervals;

converting X-ray quanta of the applied X-rays into first count signals while the first threshold value is applied;

storing the first count signals in the counting, digital X-ray detector;

setting a second threshold value of the at least one threshold value in the counting, digital X-ray detector for each of at least one second sub-time interval of the plurality of sub-time intervals;

converting X-ray quanta of the applied X-rays into second count signals while the second threshold value is applied;

storing the second count signals in the counting, digital X-ray detector;
reading the energy selective image data from the counting, digital X-ray detector; and
displaying or storing the energy selective image data,
wherein lengths of the plurality of sub-time intervals are determined based on mean expected count rates relating to the respective threshold values during the plurality of sub-time intervals.

2. The method of claim 1, wherein the lengths of the plurality of sub-time intervals are based in each case on an inverse of the mean expected count rates relating to the respective threshold values during the plurality of sub-time intervals.

3. The method of claim 1, wherein the lengths of the plurality of sub-time intervals are equal.

4. The method of claim 1, wherein the at least one threshold value is modifiable and is retrievably stored in each pixel element of the plurality of pixel elements before the application of the X-rays.

5. The method of claim 1, wherein the storing of the first count signals and the storing of the second count signals comprises transmitting count signals for each pixel element that has been acquired for each sub-time interval from the memory unit into a further memory unit directly after expiry of the sub-time interval.

6. The method of claim 5, wherein the storing of the first count signals and the storing of the second count signals in the counting, digital X-ray detector includes transmitting count signals for each pixel element that has been acquired for each sub-time interval from the further memory unit to peripherals within the subsequent sub-time interval.

7. The method of claim 1, wherein the setting of the first threshold value and the setting of the second threshold value in the counting, digital X-ray detector for a sub-time interval comprises adjusting the respective threshold value, wherein the adjusting is specific to each pixel element.

8. The method of claim 1, wherein the setting of the first threshold value and the setting of the second threshold value comprises setting a lower energy threshold, above which the incoming signal is counted, and an upper energy threshold, below which the incoming signal is counted.

9. The method of claim 1, wherein for each pixel element of the plurality of pixel elements, at least two different modifiable threshold values are applicable simultaneously.

10. A counting, digital X-ray detector of an X-ray system for receiving energy selective image data relating to an examination object, the counting, digital X-ray detector comprising:
an X-ray converter configured for direct or indirect conversion of X-rays into an electrical signal; and
a matrix comprising a plurality of counting pixel elements,
wherein for each counting pixel element of the plurality of counting pixel elements, at least one modifiable threshold value, above which an incoming signal is counted by a memory unit, is applicable,
wherein the counting, digital X-ray detector is configured to set a first threshold value for a first sub-time interval and set a second threshold value for each of at least one second sub-time interval,
wherein lengths of the plurality of sub-time intervals are determined based on mean expected count rates relating to the respective threshold values during the plurality of sub-time intervals,
wherein the X-ray converter is configured to convert X-ray quanta into first count signals while the first threshold value is applied, the first count signals being stored in the counting, digital X-ray detector, and is configured to convert the X-ray quanta into second count signals while the second threshold value is applied, the second count signals being stored in the counting, digital X-ray detector, and
wherein the counting, digital X-ray detector is further configured to read energy selective image data related to the first count signals and the second count signals.

11. The counting X-ray detector of claim 10, further comprising:
at least one digital-to-analog converter (DAC) that is configured to apply, within a time interval that includes a plurality of sub-time intervals, the first threshold value on at least one counting pixel element of the plurality of counting pixel elements in the first sub-time interval, and the second threshold value on at least one counting pixel element of the plurality of counting pixel elements in the at least one second sub-time interval.

12. The counting, digital X-ray detector of claim 11, wherein the at least one DAC comprises at least two DACs for simultaneous setting of at least two modifiable threshold values.

13. The counting, digital X-ray detector of claim 10, wherein each counting pixel element of the plurality of counting pixel elements includes a memory unit for storage of the first threshold value and the second threshold value.

14. The counting, digital X-ray detector of claim 13, wherein each counting pixel element of the plurality of counting pixel elements includes a further memory unit for intermediate storage of the first count signals and the second count signals.

15. An X-ray system for X-ray imaging, the X-ray system comprising:
an X-ray tube configured to emit X-rays that irradiate an examination object during at least one time interval that includes a plurality of sub-time intervals,
a counting, digital X-ray detector comprising:
an X-ray converter for direct or indirect conversion of X-rays into an electrical signal; and
a matrix comprising a plurality of counting pixel elements, wherein for each pixel element of the plurality of counting pixel elements, at least one modifiable threshold value, above which each incoming signal is counted by a memory unit, is applicable;
a system controller configured to control the X-ray system;
a computer configured to determine lengths of the plurality of sub-time intervals; and
an imaging system configured to process and display image data,
wherein the counting, digital X-ray detector is configured to set a first threshold value for a first sub-time interval of the plurality of sub-time intervals and set a second threshold value for each of at least one second sub-time interval of the plurality of sub-time intervals,
wherein the lengths of the plurality of sub-time intervals are determined based on mean expected count rates relating to the respective threshold values during the plurality of sub-time intervals,
wherein the X-ray converter is configured to convert X-ray quanta into first count signals while the first threshold value is applied, the first count signals being stored in the counting, digital X-ray detector, and is configured to convert the X-ray quanta into second count signals while the second threshold value is applied, the second count signals being stored in the counting, digital X-ray detector, and wherein the counting, digital X-ray detector is further configured to read energy selective image data related to the first count signals and the second count signals.

16. The X-ray system of claim 15, wherein the lengths of the plurality of sub-time intervals are based in each case on an inverse of the mean expected count rates relating to the respective threshold values during the plurality of sub-time intervals.

17. The X-ray system of claim 15, wherein the lengths of the plurality of sub-time intervals are equal.

18. The X-ray system of claim 15, wherein the first threshold value and the second threshold value are retrievably stored in each pixel element of the plurality of pixel elements before the application of X-rays.

* * * * *